United States Patent

Balduf et al.

[11] Patent Number: 5,808,123
[45] Date of Patent: Sep. 15, 1998

[54] CONTINUOUS METHOD OF PRODUCING γ-AMINOPROPYLTRIALKOXYSILANES

[75] Inventors: Torsten Balduf, Hanau; Stefan Wieland, Offenbach; Wolfgang Lortz, Wächtersbach, all of Germany; Joachim Pohlisch, Mobile, Ala.; Thomas Göbel; Horst Grethe, both of Hanau, Germany

[73] Assignee: Degussa Aktiengesellschaft, Frankfurt am Main, Germany

[21] Appl. No.: 990,730

[22] Filed: Dec. 15, 1997

[30] Foreign Application Priority Data

Dec. 18, 1996 [DE] Germany ............... 196 52 642.6

[51] Int. Cl.⁶ ........................................................ C07F 7/10
[52] U.S. Cl. ................................................................ 556/413
[58] Field of Search ............................................... 556/413

[56] References Cited

U.S. PATENT DOCUMENTS

| | | | |
|---|---|---|---|
| 2,832,754 | 4/1958 | Jex et al. | 556/413 |
| 2,920,095 | 1/1960 | Jex et al. | 556/413 |
| 3,646,087 | 2/1972 | Bennett et al. | 556/413 |
| 4,234,502 | 11/1980 | Kappler et al. | 556/413 |
| 4,234,503 | 11/1980 | Kappler et al. | 556/413 |
| 5,698,726 | 12/1997 | Rauleder et al. | 556/413 |

*Primary Examiner*—Paul F. Shaver
*Attorney, Agent, or Firm*—Beveridge, DeGrandi, Weilacher & Young, L.L.P.

[57] ABSTRACT

A continuous method of producing γ-aminopropyltrialkoxysilanes as well as mixtures of primary and secondary aminosilanes by reacting γ-chloropropyltrialkoxysilane with ammonia is disclosed. The steps are:

a) γ-chloropropyltrialkoxysilane and ammonia are first mixed in the desired amount ratio, b) this mixture is heated to the reaction temperature, c) allowed to run through a pressure reactor with a dwell time sufficient for the complete reaction, during which the mixture can run through several temperature zones, d) the reaction mixture is subsequently cooled off, e) the product (γ-aminopropyltrialkoxysilanes or the mixtures) is separated out of a two-phase mixture and f) the ammoniacal phase returned into the reactor.

12 Claims, No Drawings

CONTINUOUS METHOD OF PRODUCING γ-AMINOPROPYLTRIALKOXYSILANES

INTRODUCTION AND BACKGROUND

The present invention is relates to a method of producing γ-aminopropyltrialkoxysilanes, especially γ-aminopropyltriethoxysilanes, as well as mixtures of primary and secondary aminosilanes by reacting γ-chloropropyltrialkoxysilane with ammonia under pressure.

In principle, the reaction of γ-chloropropyltrialkoxysilane with ammonia is a known reaction. However, heretofore this reaction has been carried out only on a batchwise operation.

Accordingly, it is an object of the present invention to overcome disadvantages in a batchwise operation.

It is a further object of the present invention to carry out the reaction of γ-chloropropyltrialkoxysilane with ammonia in a continuous way.

SUMMARY OF THE INVENTION

In achieving the above and other objects, one feature of the invention is a continuous method of producing γ-aminopropyltrialkoxysilanes as well as mixtures of primary and secondary aminosilanes by reacting γ-chloropropyltrialkoxysilane with ammonia, by a series of steps including:

a) γ-chloropropyltrialkoxysilane and ammonia are first mixed in the desired amount ratio to form a single phase mixture, b) this single phase mixture is heated to the reaction temperature, c) the single phase mixture is allowed to run through a pressure reactor with a dwell time sufficient for the complete reaction, during which the reaction mixture runs through several temperature zones if necessary, d) the reaction mixture is subsequently cooled off, and an organic solvent which functions as an extraction agent added, if necessary, e) the desired product (γ-aminopropyltrialkoxysilanes or the mixtures) is separated out of the forming two-phase mixture which is formed, optionally by extraction, and f) the ammoniacal phase returned into the reactor stage (c) or into the initial mixing step (a).

DETAILED DESCRIPTION OF INVENTION

An advantage of the present invention and the continuous process described in further detail herein compared to batch methods with the same excess of ammonia, is that the method in accordance with the invention results in a lesser holdup in the system. This makes it possible to use higher excesses of ammonia and thus to shift the product composition in a purposeful manner in the direction of primary amines if this is desired. The reaction of the invention takes place under pressure, as does the mixing of the components and the extraction step. In general, the method is performed at a pressure of 5 to 60 bar, preferably 40 to 60 bar for the reaction and preferably 5 to 30 bar for the extraction step. The reaction temperature is 50° to 170° C., preferably 60° to 110° C., optionally with different temperature zones being passed through in the course of the reaction. At temperatures of up to 110° C., the reaction remains partially at the stage of the formation of γ-aminopropyltrialkoxysilane hydrochloride. This reduces the formation of the secondary amine (bis(trialkoxysilylpropyl)amine) and increases the selectivity of the reaction to form the primary amine. At temperatures greater than 110° C. the γ-aminopropyltrialkoxysilane hydrochloride reacts with ammonia to form ammonium chloride and γ-aminopropyltrialkoxysilane, so that the reaction can be advantageously carried out in a reactor with at least two temperature zones; that is, one stage below 110° C. and one stage above 110° C. The reaction of the hydrochloride with ammonia after the complete conversion of the γ-chloropropyltrialkoxysilane is especially advantageous since γ-aminopropyltrialkoxysilane can then be selectively produced.

Short-chain alkoxy compounds, preferably the ethoxy or methoxy compounds, are selected as alkoxy compounds. They are contained in the homogeneous initial mixture supplied to the reactor in a molar ratio of 1:10 to 1:300, especially 1:30 to 1:100 relative to the liquid ammonia fed in. That is to say that ammonia is always present in a distinct excess in the process of this invention.

The formation of the primary aminosilanes preferably takes place at higher excess of ammonia (1:30 and higher) whereas primary and secondary aminosilanes form in comparable constituent amounts at excess in a range of 1:10. Even these mixtures are economically advantages.

By the recycling of at least one part of the ammonia loaded with ammonium chloride (step f, ammoniacal phase), a desired concentration of ammonium chloride can be obtained in the reactor.

This concentration is to be regulated via the amount of the recycled phase and should be controlled so that no solid precipitates and that the mixture remains as a single phase during the reaction. In a two-phase reaction the amount of secondary and tertiary amines in the product increases. It is preferable to select an ammonium chloride concentration of up to 55% by weight, especially 10 to 40% by weight relative to the amount of the reaction mixture in the reactor.

The type of reactor to be used in accordance with the present invention is not limited to certain models. However, the chosen reactor must assure a dwell time, mixing and thermal transfer sufficient for the reaction to proceed to its desired conclusion. It is preferable to use tubular reactors or columns with packing bodies or structured packings. Such reactors are well known in the art.

Two phases readily form during the cooling of the reaction mixture at the reactor outlet to 10° to 60° C., as a function of the ammonium chloride content, so that the separation of the desired product can take place in a one-stage extractor (e.g. mixer settler apparatus).

One phase mainly contains the product whereas the other phase consists essentially of ammonia and ammonium chloride and is recycled.

This one-stage embodiment of the invention has an effect preferably in the case of ammonium chloride concentrations of approximately 25% by weight and higher relative to the reaction mixture.

The separation into the resulting two phases can be improved by the addition e.g. of alkanes such as n-hexane or n-heptane.

In the case of contents of approximately 25% by weight and less the phase separation no longer takes place solely on account of the temperature drop but must be assisted or brought about by the addition of the organic solvents named above. In this instance a multi-stage extractor is required.

In a preferred embodiment a partial stream of the ammoniacal phase is removed after the separation of the phase containing the product or the product mixture, and, if necessary, also organic solvents. The partial stream is directly expanded, the released ammonia re-condensed and compressed, returned into the process (step a or c) and the precipitated ammonium chloride separated off.

In this embodiment the organic phase from the extraction stage can be recovered by direct distillation. At first, the extraction agent is separated off under a vacuum and then the aminosilanes are isolated. This can be carried out in an especially cost-effective manner after the method of the invention has been carried out because the desired aminosilanes or their mixtures are contained in the reaction mixture in a very high percentage.

According to a further advantageous embodiment a partial stream is readily branched off before the cooling off of the reaction mixture and is brought in contact with the phase containing the product or product mixture after step e) without pressure or at a pressure of up to 10 bar.

Vapors consisting of ammonia and the organic solvent used in the system form thereby which are separated in a column and returned to the process at the appropriate places.

At a content of 10 to 40% by weight ammonium chloride in the reaction mixture 5 to 30% by volume of this mixture is removed relative to the total volume of this mixture. The reaction mixture contains ammonia, ammonium chloride and the aminosilanes as well as, optionally, non-reacted chloroalkylsilane.

The volatile components such as e.g. ammonia are removed from this phase in this manner, the ammonium chloride accumulates in solid form and can be separated by known procedures from the organic phase.

After the separation of the solid from the organic phase the filtrate is readily subjected to the distillation described under a vacuum. Since the part of the ammoniacal phase (step f) to be returned is returned in liquid form according to the invention the amount of ammonia to be evaporated is reduced in comparison to a batchwise production.

The following examples will serve to illustrate the invention:

EXAMPLE 1

γ-aminopropyltriethoxysilane is obtained in a γ-chloropropyltriethoxysilane-ammonia ratio of 1:100 at p=50 bar, in a first reaction at 100° C. and a post reaction at 120° C. in a yield of up to 95% relative to the crude silane mixture obtained from primary, secondary and tertiary aminosilanes. If γ-chloropropyltriethoxysilane and ammonia are used in a ratio of 1:11 at P=56 bar and T=95° C. the typical composition of the product is 48.7% by weight primary and 46.5% by weight secondary and 4.8% by weight tertiary aminosilane.

EXAMPLE 2

At a concentration of ammonium chloride of 45% by weight relative to the ammoniacal phase 0.212 kg/h ammonia and 0.028 kg/h amino silane are mixed with 0.084 kg/h n-heptane in a mixer. 97.8% of the aminosilane used is discharged with the organic phase out of a one-stage extractor at 20° C. and 8.6 bar.

EXAMPLE 3

The extraction is carried out at 25% by weight ammonium chloride in the ammoniacal phase with a product stream of 0.335 kg/h ammonia and 0.044 kg/h aminosilane in an extraction column 60° C. and 26 bar. 96.2% of the aminosilane used is determined in the extract phase at an n-heptane stream of 0.335 kg/h.

Further variations and modifications of the foregoing will be apparent to those skilled in the art and are intended to be encompassed by the claims appended hereto.

German priority application 196 52 642.6 is relied on and incorporated herein by reference.

We claim:
1. A continuous method of producing an γ-aminopropyltrialkoxysilane comprising:
   a) mixing together an γ-chloropropyltrialkoxysilane and ammonia to form a reaction mixture;
   b) heating said mixture to a sufficient reaction temperature, wherein the γ-chloropropyltrialkoxysilane will react with ammonia;
   c) allowing said mixture to run through a pressure reacting zone with a dwell time sufficient for complete reaction, during which the mixture can run through several temperature zones;
   d) cooling the reaction mixture and optionally adding, an organic solvent to form a two-phase mixture;
   e) separating said γ-aminopropyltrialkoxysilane out of the two-phase mixture formed, optionally by extraction; and
   f) returning an ammoniacal phase to the reaction mixture in (a).

2. The method according to claim 1, wherein said reaction temperature is 50° to 170° C.

3. The method according to claim 2, wherein said reaction zone includes a first temperature zone at 60° to 110° C. to produce an γ-aminopropyltrialkoxysilane hydrochloride which is reacted with ammonia in a second temperature zone at greater than 110° C. to form γ-aminopropyltrialkoxysilane and ammonium chloride.

4. The method according to claim 1, further comprising separating a partial stream off after step e, and separating off the ammonium chloride produced and returning the ammonia to step a).

5. The method according to claim 1, further comprising separating a partial stream before step d after the reaction zone and optionally bringing it into contact with cooled-down and separated phase containing the product and optionally extracting.

6. The method according to claim 1, wherein a two-phase area is adjusted by lowering the temperature and/or by adding an organic solvent.

7. The method according to claim 6, wherein a liquid alkane is used as the solvent.

8. The method according to claim 7, wherein n-hexane or n-heptane is the liquid alkane.

9. The method according to claim 1, wherein the γ-chloropropyltrialkoxysilane and the ammonia are used in a molar ratio of 1:10 to 1:300.

10. The method according to claim 9, wherein the molar ratio is from 1:30 to 1:100.

11. The method according to claim 1 wherein the reaction is carried out in the presence of up to 55% by weight ammonium chloride.

12. The method according to claim 1 wherein γ-chloropropyltriethoxysilane or -trimethoxysilane is reacted.

* * * * *